United States Patent
Hinrichs et al.

(10) Patent No.: US 6,841,169 B2
(45) Date of Patent: Jan. 11, 2005

(54) STABILIZER FOR PHARMACONS

(75) Inventors: Wouter Leonardus Joseph Hinrichs, Groningen (NL); Henderik Willem Frijlink, Eelde (NL)

(73) Assignee: Rijksuniversiteit Groningen, Groningen (NL)

(*) Notice: Subject to any disclaimer, the term of this patent is extended or adjusted under 35 U.S.C. 154(b) by 118 days.

(21) Appl. No.: 10/007,800

(22) Filed: Dec. 7, 2001

(65) Prior Publication Data

US 2002/0122825 A1 Sep. 5, 2002

(51) Int. Cl.[7] ............... A61K 9/14; A61K 9/20; A61K 9/48; A61K 7/00; A61F 2/00

(52) U.S. Cl. ............... 424/493; 424/401; 424/423; 424/426; 424/433; 424/436; 424/451; 424/458; 424/464; 424/489; 424/490; 514/951

(58) Field of Search ............... 424/451, 464, 424/489, 423, 426, 436, 493, 401, 433, 458, 490

(56) References Cited

U.S. PATENT DOCUMENTS

| 5,250,429 A | 10/1993 | Jolly et al. ............ 435/196 |
| 6,455,068 B1 * | 9/2002 | Licari ............ 424/464 |

FOREIGN PATENT DOCUMENTS

| EP | 0 383 569 A | 8/1990 | |
| EP | 0 437 632 | 7/1991 | |
| EP | 0879600 A1 * | 11/1998 | ......... A61K/31/715 |
| JP | 61181960 A * | 8/1986 | ............ A61K/7/03 |
| JP | 07099965 A * | 4/1995 | ......... A61K/35/12 |
| WO | 96/05809 A | 2/1996 | |

* cited by examiner

Primary Examiner—James M. Spear
(74) Attorney, Agent, or Firm—Banner & Witcoff, Ltd.

(57) ABSTRACT

The present invention relates to an auxiliary substance for an active substance, such as a pharmacon. The auxiliary substance has a stabilizing action. The auxiliary substance further has a positive influence on the bioavailability of the active substance with which the auxiliary substance can be incorporated into a pharmaceutical preparation. The auxiliary substance is based on a fructan having a number-average degree of polymerization of at least 6 and is used in the form of a sugar glass.

21 Claims, 2 Drawing Sheets

Figure I
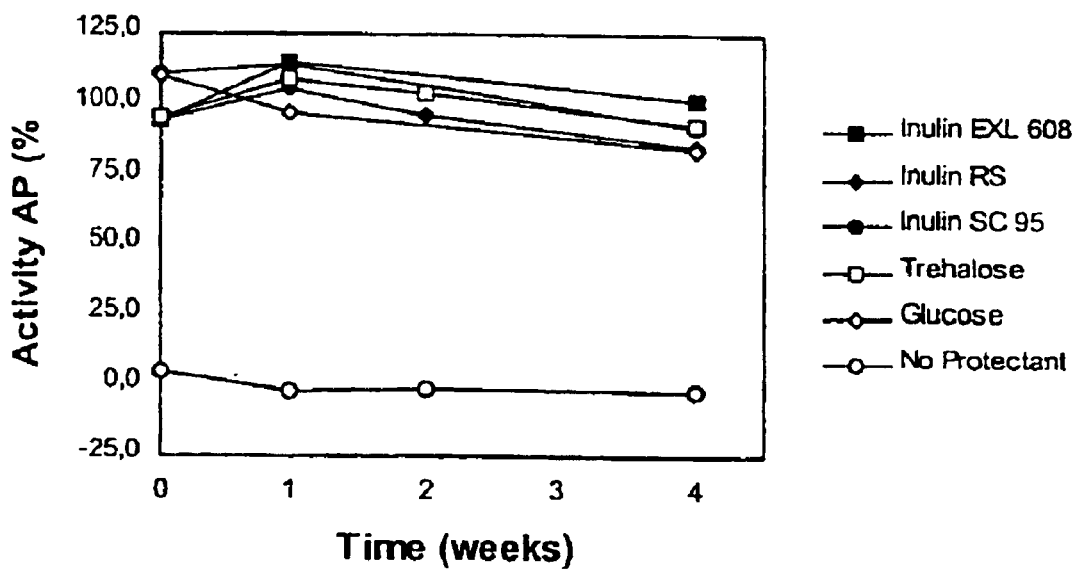
Figure II
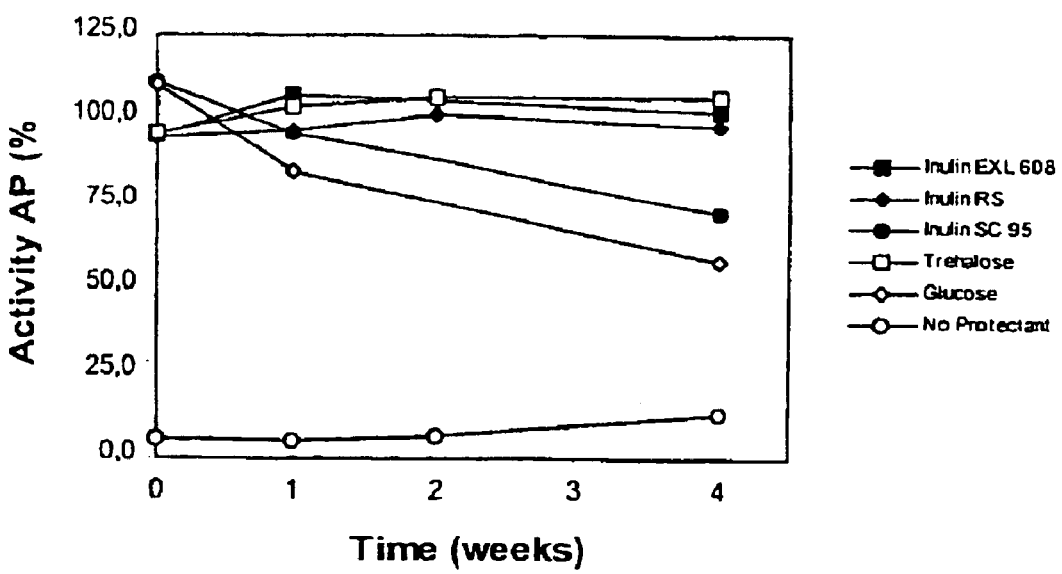

Figure III
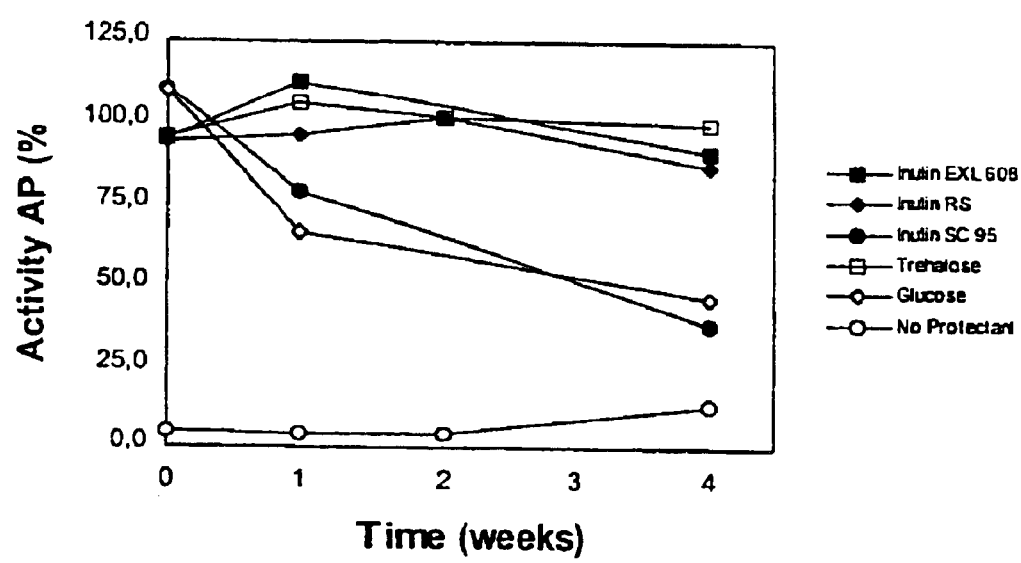

STABILIZER FOR PHARMACONS

RELATED APPLICATIONS

The application is a continuation of PCT Application No. PCT/NL00/00405, designating the United States and filed Jun. 13, 2000; which claims the benefit of the filing date of Netherlands Application No. NL 1012300, filed Jun. 11, 1999, both of which are hereby incorporated herein by reference.

This invention relates to a stabilizer for pharmacons, and to a method for stabilizing a pharmacon with such stabilizer.

Through the developments in biotechnology, we have an increasingly greater variety of therapeutic proteins and peptides at our disposal. It is to be expected that the application of these proteins and peptides in medicine will increase strongly in the future.

In the production, therapeutic proteins and peptides are obtained as aqueous solutions. The problem is that proteins and peptides in solution are normally not stable. As a consequence, the biological activity of the proteins and peptides is gradually lost, so that the shelf-life of these products is limited. Various chemical and physical mechanisms are responsible for the decrease of the activity. Chemical mechanisms are inter alia hydrolysis, deamination, oxidation, racemization and disulfide exchange. Physical mechanisms are inter alia aggregation, gelling, denaturation and adsorption.

It can be inferred from the above that the decrease of the activity is to be imputed in particular to the aqueous environment of the protein or peptide. In other words, if the product could be obtained in dry form, the shelf-life of the product would be extended. The protein or peptide can be obtained in dry form by, for instance, freeze-drying, vacuum-drying or spray-drying. However, during the drying process, the protein or peptide is exposed to strong mechanical forces (for instance during the freezing of a solution in preparation for freeze-drying), which also causes damage to the protein or peptide. This damage can be prevented by adding a stabilizing auxiliary substance to the solution. With the right choice of the auxiliary substance and the right drying procedure, the auxiliary substance will also stabilize the product in the dry form, thereby extending shelf-life still further.

Not only therapeutic proteins and peptides, but also many other pharmacons are unstable. For comparable reasons as mentioned above, their shelf-life can be prolonged by drying the product in the presence of a suitable auxiliary substance.

BRIEF DESCRIPTION OF THE DRAWINGS

FIGS. 1–3 show how freeze drying affects the activity of products according to the invention.

Most pharmacons are processed into non-intravenous forms of administration such as tablets, capsules, suppositories, lozenges, dermatics and suspensions for subcutaneous or intramuscular injections. To achieve adequate bioavailability, it is necessary that the medicine eventually becomes available in dissolved form at an adsorption membrane. However, many pharmacons are poorly soluble in aqueous medium. As a consequence, the rate of dissolving is normally low, which leads to the bioavailability being low as well. Through the choice of a suitable auxiliary substance, the rate of dissolving and hence the bioavailability can be increased.

Now, the object of the invention is to provide an auxiliary substance which can be used for stabilizing sensitive pharmacons. This group of sensitive pharmacons extends not only to proteins and poly)peptides, but also to other active substances such as bioactive or pharmaceutically active substances, among which vitamins, whose stability may be at stake when the active substance is being processed into a suitable form of administration, such as a tablet. It is also an object of the invention for the auxiliary substance contemplated to contribute to the increase of the bioavailability of an active substance which, together with the auxiliary substance, is present in a form of administration.

Known stabilizers that protect pharmacons during the drying procedure are sugars. Sugars protect the pharmacon because the hydroxyl groups of sugars replace the water molecules which form hydrogen bridges with the pharmacons. This is sometimes called the "water replacement theory". In a manner of speaking, a coating of sugar molecules is provided around the pharmacon, which protects the pharmacon from harmful influences during drying.

In dry form, a sugar coating also affords protection to the pharmacon if the sugar is in the glass state. In the glass state, the molecules are oriented more or less randomly with respect to each other, and the mobility of the molecules is very low. Because of the random orientation, this state is sometimes referred to as amorphous state instead of glass state. Because the orientation of the sugar molecules is more or less random, the interactions of the hydroxyl groups of the sugar and the pharmacon remain intact and protection is thereby maintained. The low mobility of the sugar molecules is of great importance since, as a consequence, the mobility of the pharmacon is very low as well. As a result, any degenerative processes are strongly delayed.

When during the drying procedure the sugar crystallizes, the protective action is lost. The fact is that during crystallization, phase separation between the sugar and the pharmacon takes place, and the interactions between sugar and the pharmacon are broken. Not only is the protection lost as a result, but also the pharmacon may be damaged during the phase separation process itself.

Accordingly, special requirements are imposed on the drying procedure so as to prevent crystallization. In the literature, often small sugars are described for the use as sugar glass. However, small molecules normally crystallize much faster than large ones.

According to the present invention, presently a specific fructan is used for forming a sugar glass around an active substance, such as a pharmacon. It has been found that a fructan having a number-average degree of polymerization of at least 6 has a particularly good stabilizing action and also positively influences the bioavailability of the active substance with which it is incorporated into a form of administration.

It is noted, incidentally, that it is known from international patent application 96105809 that particular sugars are suitable for stabilizing a pharmacon. The publication describes a method for stabilizing bioactive substances, such as proteins, in which an aqueous suspension or solution of a sugar and the bioactive substance is dried by, for instance, freeze-drying, spray-drying or vacuum-drying. As examples for suitable sugars, various substances are mentioned, among which inulin as sole fructan. However, no origin or properties of the inulin used are mentioned. Many commercially available inulins have a number-average degree of polymerization of less than 6. From the experiments described, it appears that the inulin examined is not capable of keeping the restriction enzyme PstI active for 7 days at 37° C.

European patent application 0 383 569 discloses that materials which are unstable per se can be kept stable by means of a carrier material which is soluble or swellable in water and which is in a glassy or rubbery condition. Although this carrier material can be a sugar, synthetic polymers such as polyvinylpyrrolidone, polyacrylamide or polyethyleneimine are preferred. In Example 13 of the document, the use of a vacuum-dried inulin for stabilizing the enzyme lactate dehydrogenase is described. It is unclear what the number-average degree of polymerization of this inulin is. It is striking, further, that the conditions during storage of the samples described are so ideal that even without carrier material destabilization would hardly be expected. The samples were preserved at 25° C. and low air humidity. It is also striking that the experiments described do not comprise a control test, i.e., a test of the enzyme without carrier material.

According to the invention, the term pharmacon is understood to mean a biologically or pharmaceutically active substance. The substance is capable of accomplishing a biological effect. The pharmacon can be of natural origin, but may also have been prepared synthetically or semisynthetically. It is noted here that intermediaries of such a preparation also fall within the concept of pharmacon. Examples of pharmacons are cells, viruses, plasmids, nucleic acids such as DNA and RNA, nucleotides, oligosaccharides, proteins and peptides, amino acids, vitamins, lipids, hormones, enzymes, growth factors, antibodies, and antigens. Metabolites of the substances mentioned, that is, substances that are formed in vivo by an organism after administration of one or more of the substances formed are also encompassed by the term pharmacon. The invention is applicable in particular in the stabilization of peptides and proteins.

A fructan is understood to mean any oligo- or polysaccharide which contains a plurality of anhydrofructan units. The fructans can have a polydisperse chain length distribution, and can have a straight or branched chain. Branched fructans are often designated as glucans. In the context of the present invention, these substances are also understood to fall within the term fructans.

Preferably, the fructans contain mainly β-1,2 bonds, as in inulin, but they can also contain β-2,6 bonds, as in levan. Suitable fructans can originate directly from a natural source, but may also have undergone a modification. Examples of modifications in this connection are reactions known per se that lead to a lengthening or shortening of the chain length.

An important parameter of fructans suitable according to the invention is the average chain length (number-average degree of polymerization, $DP_n$). It should be at least 6 and will normally not be greater than about 1,000. Preferably, a fructan is used having a $DP_n$ of at least 7, more preferably at least 10, still more preferably at least 14, up to about 60. According to the invention, the $DP_n$ can be determined by means of High Pressure liquid Chromatography (anion exchange HPLC).

Fructans that are suitable according to the invention are, in addition to naturally occurring polysaccharides, also industrially prepared polysaccharides, such as hydrolysis products, which have shortened chains, and fractionated products having a modified chain length, in particular having a $DP_n$ of at least 6. A hydrolysis reaction to obtain a fructan having a shorter chain length can be carried out enzymatically (for instance with endoinulinase), chemically (for instance with aqueous acid), physically (for instance thermally) or by the use of heterogeneous catalysis (for instance with an acid ion exchanger). Fractionation of fructans, such as inulin, can be achieved inter alia through crystallization at low temperature, separation with column chromatography, membrane filtration, and selective precipitation with an alcohol Other fructans, such as long-chain fructans, can be obtained, for instance through crystallization, from fructans from which mono- and disaccharides have been removed, and fructans whose chain length has been enzymatically extended can also serve as fructan that is used in the present invention. Further, reduced fructans can be used. These are fructans whose reducing end groups, normally fructose groups, have been reduced, for instance with sodium borohydride or hydrogen in the presence of a transition metal catalyst. Fructans which have been chemically modified, such as crosslinked fructans and hydroxyalkylated fructans, can also be used.

In a preferred embodiment, the fructan that is used according to the invention is inulin. Inulin is a polysaccharide, consisting of β-1,2 bound fructose units with an α-D-glucopyranose unit at the reducing end of the molecule. The substance occurs inter alia in the roots and tubers of plants of the Liliaceae and Compositae families. The most important sources for the production of inulin are the Jerusalem artichoke, the dahlia and the chicory root. Industrial production of inulin starts mainly from the chicory root. The chief difference between inulin originating from the different natural sources resides in the degree of polymerization, which can vary from about 6 in Jerusalem artichokes to 10–14 in chicory roots and higher than 20 in the dahlia.

Inulin is an oligosaccharide which in amorphous condition has favorable physicochemical properties for the application as auxiliary substance for pharmaceutical forms of administration. These physicochemical properties are: (adjustable) high glass transition temperature, low hygroscopicity, no (reducing) aldehyde groups and probably a low rate of crystallization. In addition, inulin is not toxic and not expensive.

When a solution of inulin is dried, for instance by freeze-drying, vacuum-drying or spray-drying, amorphous inulin can be obtained. It has been found that if further a pharmacon is present in the solution, it is protected by inulin from harmful influences during drying, and that after the drying process the pharmacon is surrounded by a protective coating of amorphous inulin. As a result, it will be possible to considerably lengthen the shelf-life of unstable pharmacons, such as therapeutic proteins and peptides. In addition, with such a coating the bioavailability of poorly soluble pharmacons could be raised considerably.

It can be concluded that amorphous inulin is of great interest as an auxiliary substance for preparations for pulmonary administration, oral administration, parenteral administration, suppositories, enemas and dermatics.

Below, the invention is further elucidated with reference to the fructan inulin. This is not to be construed as limiting the invention.

As mentioned hereinabove, poorly soluble pharmacons can have a low bioavailability when they are incorporated into tablets for, for instance, oral or rectal administration. If such a pharmacon is enclosed in an inulin glass, each pharmacon molecule is provided with a coating of amorphous inulin. In other words, the pharmacon is in a monomolecular form. Since amorphous inulin dissolves rapidly, the rate of dissolving of the enclosed pharmacon will also be strongly increased. As a consequence, also the rate of absorption and hence the bioavailability will be increased.

The high rate of dissolving can also have advantages in other forms of administration. For instance in pulmonary administration, when a very rapid uptake is desired.

When molten sugar is slowly cooled, crystallization takes place at a particular temperature. If, on the other hand, molten sugar is cooled rapidly, the glass transition temperature (Tg) is passed. The Tg is always lower than the crystallization or melting temperature. The glass transition is characterized by a strong decrease of the mobility of the molecules, while the orientation of the molecules remains unchanged. The crystal structure is thermodynamically stabler than the glass condition. However, the mobility of the molecules in glass is so low that crystallization proceeds so slowly that this is not measurable. However, if the temperature is raised above the Tg but below the melting temperature, the mobility of the molecules is such that crystallization can take place fairly rapidly.

It is therefore of great importance that the temperature of a pharmacon stored in a sugar glass be lower than the Tg to prevent crystallization of sugar and hence to preserve protective action. Now, the Tg of a sugar is normally higher than room temperature. As noted, in the literature, in particular small sugars, such as sucrose, trehalose and mannitol, are mentioned as material for sugar glasses. Because of the high Tg (ca 120° C.), trehalose comes out in many scientific publications as a promising candidate (most sugars have a lower Tg). The Tg of fructans, in particular of inulin, increases with increasing molecular weight, so that, within particular limits, the Tg can be set. In experiments, values of 140 and 155° C. were found for inulins having a number-average/weight-average degree of polymerization ($DP_n$/$IDP_w$) of 14.2/19.4 and 23.0126.2, respectively. In other words, the Tg's of some inulins are clearly higher than those of trehalose. This shows that inulins are very promising for the formation of a sugar glass for stabilizing active substances, such as pharmacons.

In practice, a sugar glass will never be completely anhydrous. This is for instance the consequence of uptake of water from the air. Uptake of water has a substantial effect on the Tg: the Tg is strongly lowered according as more water is taken up. The extent of water uptake depends on the hygroscopicity of the material and of the relative degree of air humidity. It was found that trehalose glass that was exposed at 20° C. to a relative air humidity of 45% first deliquesced (that is, the Tg falls below 20° C.) and then crystallized. Glasses manufactured from inulin having a $DP_n$/$DP_w$ of 14.2119.4, by contrast, did permit of storage under these conditions without deliquescence being observed. Inulin glasses having a $DP_n$/$DP_w$ of 23.0/26.2 that were left to stand at 20° C. remained intact at a relative air humidity as high as 60%.

It can be concluded from this that inulin glasses can be stored at a much higher relative degree of air humidity than trehalose without the Tg being passed.

For forming a sugar glass based on a fructan, different procedures can be followed.

In the case of freeze-drying, a solution is rapidly cooled, so that only crystallization of water (ice formation) takes place. During this process, the residual solution becomes more and more concentrated. This process is also referred to as "freeze-concentration". At some point, the concentrated solution passes the glass transition temperature. This is also referred to as Tg'. Thus a glass is formed consisting of part sugar and part water. Thereafter, the pressure is reduced so that first the water sublimes from the ice crystals and then water from the glass. This yields a porous cake consisting of a sugar glass. A porous cake is desirable because it can be rapidly reconstituted.

Freeze-drying can go wrong in two ways. Firstly: when the solution is cooled too slowly, not only water but also the sugar crystallizes. When an unstable pharmacon is present, the protective action is lost as a result. Secondly: when sublimation takes place at a temperature higher than the Tg', no glass is formed. After the sublimation of water from the ice crystals, evaporation of water (no sublimation!) from the freeze-concentrated solution takes place. As a result, the cake collapses, as it were, and crystallization of the sugar can still take place.

This last was tested in experiments with trehalose and inulin. Freeze-drying was done at a sample temperature of −16° C. With trehalose, a collapsed cake was found, while in inulin $DP_n$/$DP_w$ of 14.2/19.4 a fine porous cake was formed. This shows that the Tg' of trehalose is clearly lower than for inulin $DP_n$/$DP_w$ of 14.2119.4. Accordingly, inulin can be freeze-dried under less stringent conditions.

In vacuum-drying, the pressure above a solution at room temperature is lowered, so that the water evaporates. Because during evaporation heat is drawn from the environment, the temperature must be properly conditioned to prevent freezing. In addition, what is to be prevented is that under the influence of the low pressure the solution starts to boil. The fact is that when a protein is present, due to the increased liquid/air surface, denaturation will readily occur. The great risk of this technique is that instead of glass formation, crystallization may take place. The advantage of inulin here is that crystallization occurs less readily than in small sugars.

In spray-drying, a solution is atomized in a stream of hot air. Through the evaporation of water, small particles are formed. These can have a size of 1–5 μm and are therefore suitable for pulmonary administration. It is known that trehalose is a compound which is difficult to spray-dry. Inulin, by contrast, readily permits of proper spray-drying.

The products obtained with the above-described techniques, i.e., in which an active substance is incorporated in a sugar glass of a fructan, can be excellently processed into suitable forms of administration. Those skilled in the art will be able to adjust the shaping techniques, known per se, to the properties of the sugar glass, where necessary.

Many sugars such as glucose and lactose contain aldehyde groups. These reducing groups can react with amine groups of, for instance, proteins and peptides, thereby forming a Schiff's base. This initial reaction can lead to a cascade of reactions, also known as Maillard browning. The Maillard reaction may give rise to the bioactivity of the pharmacon being seriously affected and is hence highly undesirable.

An important advantage of fructans, and in particular inulin, is that due to the specific coupling of the monosaccharide units in the oligosaccharide chain, there are no aldehyde groups present and therefore the Maillard browning cannot take place.

Fructans could be used well in a large variety of forms of administration. In spray-drying, spherical particles of a diameter of 1–5 μm can be obtained. This particle size is ideal for powders for pulmonary a administration. Accordingly, by spray-drying a solution of inulin and a pharmacon, a form of administration for the lungs can be developed. To be further considered here is the incorporation of inulin glasses in which pharmacons are enclosed, into preparations for oral, pulmonary and parenteral administration. Suitable examples are inter alia suppositories, enemas, tablets, capsules, lozenges, dermatics and suspensions for subcutaneous or intramuscular injections.

Fructans, and in particular inulin, form non-toxic products and are mentioned in the Pharmacopeia. In current clinical practice, fructans are already being used, inter alia as tracer material to test renal efficiency in patients. Accordingly, from a toxicological point of view, problems with the acceptance of amorphous inulin as an auxiliary substance for pharmaceutical forms of administration are are not to be expected.

The invention will presently be elucidated further in and by the following examples.

EXAMPLE I

Determination of Molecular Weight

The molecular weight expressed in number-average degree of polymerization ($DP_n$) and weight-average degree of polymerization ($DP_w$) was determined by means of an anion exchange HPLC. For this purpose, a CarboPac PA1 (4×250 mm) column and a CarboPac PA (4×50 mm) pre-column were used. Elution was done with a 60 min linear gradient with a mixture of solutions of sodium hydroxide and sodium acetate in water whose ratio was varied from 0.10:0.025 mol/L to 0-10:040 mol/L. The system (DIONEX) included a Pulsed Electrochemical Detector. The pulse voltage used was 0.1; 0.6 and 0.6 V for 0.5; 0.1 and 0.05 sec, respectively. The signal was integrated between 0.3 and 0.5 sec after the beginning of the pulse. The system was calibrated with solutions of oligomers of known chain lengths and concentrations.

Preparation of Freeze-dried Samples

Alkaline phosphatase with and without stabilizer was dissolved in a 0.05 M 2-amino-2-methyl-1,3-propanediol solution in water, pH 9.8. The concentration of alkaline phosphatase was 2.5 mg/mL in all cases. Used as stabilizer were: inulin SC 95, inulin RS and inulin EXL 608. Trehalose and glucose were used as positive and negative control, respectively. The weight ratio of alkaline phosphatase to stabilizer was 1 to 9 in all cases. Of the solutions, 2 mL were transferred to glass sample vessels of a diameter of about 2 cm. The sample vessels were transferred to liquid nitrogen. After the solution had frozen completely, the sample vessels were transferred to a Christ freeze-drier, model Alpha 2-4, at a plate temperature of −30° C., followed by freeze-drying at a condenser temperature of −53° C. and a pressure of 0.220 mbar for 18 hours. Then, during 6 hours, the plate temperature and the pressure were gradually raised to 20° C. and 0.520 mbar, respectively. Thereafter the freeze-drying process was continued for 20 more hours.

Conditioning

Two series of experiments were carried out. In the first series, the samples were left to stand for 6 days at 0% relative humidity (RH) and 60° C., whereafter the activity of the protein was determined. In the second series of experiments, the samples were left to stand in an exsiccator above silica gel (0% RH) or in controlled-climate cabinets (45% and 60% RH) at 20° C. At different times, the activity of the protein was determined.

Determining Activity of Alkaline Phosphatase

The activity of alkaline phosphatase was determined as follows. The freeze-dried samples were reconstituted with water. To 50 μl of the solution obtained, there were added 905 μL of a 0.05 M 2-amino-2-methyl-1,3-propanediol solution in water, pH 9.8, and 20 μL of a 100 mM $MgCl_2$ solution in water. Next, 50 μL of a freshly prepared solution of 10 mg phosphatase substrate (para-nitrophenyl phosphate) per mL water were added. The mixture was vortexed and then incubated at 37° C. After 30 minutes, the reaction was stopped by addition of 5.0 mL of a 0.1 N solution of NaOH in water. The extinction of the solution obtained was measured at 405 nm. A calibration line was made using freshly prepared solutions of alkaline phosphatase in 0.05 M 2-amino-2-methyl-1,3-propanediol in water, pH 9.8, of known concentrations.

Results

As can be seen in Table I, freeze-drying an alkaline phosphatase solution led to a dramatic decrease of the activity. When three different inulins as well as the positive and negative control were used as stabilizer, however, no significant decrease of the activity occurred.

After 6 days of storage of the freeze-dried inulin SC 95, trehalose and glucose containing samples at 0% RH and 60° C., the activity of the protein was gone completely (see Table I). The activity of alkaline phosphatase of the inulin RS and inulin EXL 608, by contrast, was still substantial after 6 days under these conditions (see Table 1).

After 4 weeks of storage of all freeze-dried sugar-containing samples at 0% RH and 20° C., the activity of the protein was preserved ho completely. FIG. I shows the activity of alkaline phosphatase of freeze-dried samples after storage at 0% RH and 20° C. as a function of the storage time. Data are averages of 2 independent experiments.

This also holds for the inulin RS, inulin EXL 608 and trehalose containing samples which were left to stand for 4 weeks at 45% and 60% RH (see FIGS. II and III).

FIG. II shows the activity of alkaline phosphatase of freeze-dried samples after storage at 45% RH and 20° C. as a function of the storage time. Data are averages of 2 independent experiments.

FIG. III shows the activity of alkaline phosphatase of freeze-dried samples after storage at 60% RH and 20° C., as a function of the storage time. Data are averages of 2 independent experiments.

Storage of the inulin SC 95 and glucose containing samples under these conditions, however, led to a substantial decrease of the activity. At 45% RH the activity gradually decreased in the course of 4 weeks to 72.3±0.1% and 57.9±3.1% for inulin SC 95 and glucose, respectively. At 60% RH, after four weeks, the activity was 38.8±6.5% and 46.3±16.1% for inulin SC 95 and glucose, respectively.

Table I

| | $DP_n/DP_w$ [a,b] | Activity alkaline phosphatase directly after freeze drying (%)[c] | Activity alkaline phosphatase after freeze-drying and 6 days at 0% RH and 60° C. (%)[d] |
|---|---|---|---|
| Inulin EXL608 | 23.0/26.2 | 95.0 ± 2.5 | 50.9 ± 15.3 |
| Inulin RS | 14.2/19.4 | 94.4 ± 10.6 | 42.8 ± 10.8 |
| Inulin SC 95 | 5.5/6.0 | 110.0 ± 2.4 | −1.4 ± 1.6 |
| Trehalose | — | 95.9 ± 11.5 | −1.4 ± 2.8 |
| Glucose | — | 110.3 ± 10.6 | 0.8 ± 4.5 |
| No stabilizer | — | 5.4 ± 2.1 | −0.7 ± 0.8 |

[a]$DP_n$: number-average degree of polymerization; $DP_w$: weight-average degree of polymerization
[b]The degree of polymerization was determined by means of anion exchange HPLC.

Table I-continued

| $DP_n/DP_w^{a,b}$ | Activity alkaline phosphatase directly after freeze drying (%)$^c$ | Activity alkaline phosphatase after freeze-drying and 6 days at 0% RH and 60° C. (%)$^d$ |
| --- | --- | --- |

$^c$Average of 2 independent experiments
$^d$Average of 4 independent experiments

EXAMPLE II

A solution of 9.0 wt. % inulin RS ($DP_n$14.2; $DP_w$=19.4) and 1.0 wt. % alkaline phosphatase was prepared in 0.05 M 2-amino-2-methyl-1,3-propanediol (Ammediol), pH 9.8. The solution was spray-dried with a Buchi 190 minispray-drier. The solution was pumped at a rate of 5 mL/min and misted with an air stream of 600 L/hour. The mist was dried with an air stream of 600 L/min and an inlet temperature of 120–150° C. These conditions led to an outlet temperature of 50–80° C. The product, a very fine white powder, was stored in an exsiccator over silica gel.

What is claimed is:

1. A composition comprising a pharmacon incorporated into a fructan having a number-average degree of polymerization of at least 7 in the form of a sugar glass.

2. The composition according to claim 1, wherein the fructan has a number-average degree of polymerization of at least 10.

3. The composition according to claim 1, wherein the fructan is inulin.

4. A method for stabilizing a pharmacon, comprising incorporating a pharmacon in a sugar glass of a fructan having a number-average degree of polymerization of at least 7.

5. The method for stabilizing a pharmacon according to claim 4, wherein the fructan has a number-average degree of polymerization of at least 10.

6. The method for stabilizing a pharmacon according to claim 4, wherein the fructan is inulin.

7. The method for stabilizing a pharmacon according to claim 4, wherein the step of incorporating a pharmacon comprises forming a solution comprising a fructan and a pharmacon and drying the solution to form a sugar glass.

8. A composition produced by a process comprising incorporating a pharmacon into a sugar glass of a fructan having a number-average degree of polymerization of at least 7.

9. A pharmaceutical preparation comprising a pharmacon incorporated into a sugar glass of a fructan having a number-average degree of polymerization of at least 7.

10. The pharmaceutical preparation according to claim 9 in the form of a tablet, capsule, lozenge, dermatic, suppository, powder for pulmonary administration, or a rod or suspension for subcutaneous or intramuscular administration.

11. A method for producing a bioavailable form of a pharmacon in a pharmaceutical preparation comprising incorporating a pharmacon into sugar glass of a fructan having a number-average degree of polymerization of at least 7, wherein the bioavailability of the pharmacon is thereby increased.

12. The method for stabilizing a pharmacon according to claim 4, wherein the fructan is a glucan.

13. The method for stabilizing a pharmacon according to claim 4, wherein the fructan is levan.

14. The method for stabilizing a pharmacon according to claim 4, wherein the pharmacon is an active substance.

15. The method for stabilizing a pharmacon according to claim 4, wherein the pharmacon is selected from the group consisting of DNA, RNA, nucleotide, oligosaccharide, protein, peptide, amino acid, vitamin, lipid, hormone, enzyme, growth factor, antibody, antigen, metabolites of the above, and mixtures of the above.

16. The method for stabilizing a pharmacon according to claim 7, wherein the solution is dried by spray-drying.

17. The method for stabilizing a pharmacon according to claim 16, wherein the spray-drying produces spherical particles from between 1 to 5 μm.

18. The method for stabilizing a pharmacon according to claim 7, wherein the solution is dried by vacuum drying.

19. The method for stabilizing a pharmacon according to claim 7, wherein the solution is dried by freeze drying.

20. A pharmacon according to claim 8, wherein the pharmacon is an active substance.

21. A pharmacon according to claim 8, wherein the pharmacon is selected from the group consisting of: DNA, RNA, nucleotide, protein, peptide, amino acid, oligosaccharide, vitamin, lipid, hormone, enzyme, growth factor, antibody, antigen, metabolites of the above, and mixtures of the above.

* * * * *

UNITED STATES PATENT AND TRADEMARK OFFICE
CERTIFICATE OF CORRECTION

PATENT NO. : 6,841,169 B2
DATED : January 11, 2005
INVENTOR(S) : Wouter Leonardus Joseph Hinrichs and Henderik Willem Frijlink It is certified that error appears in the above-identified patent and that said Letters Patent is hereby corrected as shown below:

<u>Title page,</u>
Item [65], Prior Publication Data, please insert
-- PCT/NL00/00405 filed June 13, 2000
NL 1012300 filed June 11, 1999 --

Signed and Sealed this

Fifth Day of July, 2005

JON W. DUDAS
*Director of the United States Patent and Trademark Office*